(12) United States Patent
Lowe

(10) Patent No.: US 6,716,961 B2
(45) Date of Patent: Apr. 6, 2004

(54) CHIRAL PEPTIDE NUCLEIC ACIDS WITH A N-AMINOETHYL-D-PROLINE BACKBONE

(75) Inventor: Gordon Lowe, Abingdon (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 10/022,585

(22) Filed: Oct. 30, 2001

(65) Prior Publication Data

US 2003/0162699 A1 Aug. 28, 2003

(51) Int. Cl.$^7$ ................................................ A61K 38/00
(52) U.S. Cl. ................ 530/300; 530/322; 544/269; 544/277; 544/319; 536/22.1; 536/23.1; 536/24.3; 435/6
(58) Field of Search ................ 530/300, 322; 544/269, 277, 319; 536/22.1; 435/6

(56) References Cited

U.S. PATENT DOCUMENTS

| | | |
|---|---|---|
| 4,501,901 A | 2/1985 | Thottathil et al. |
| 5,623,049 A | 4/1997 | Löbberding et al. |
| 6,403,763 B1 * | 6/2002 | Lowe .................... 530/300 |

FOREIGN PATENT DOCUMENTS

| | | |
|---|---|---|
| CA | 2131760 | 3/1995 |
| EP | 0095584 | 12/1983 |
| EP | 0646596 | 4/1995 |

* cited by examiner

Primary Examiner—Ethan Whisenant
Assistant Examiner—Shar Hashemi
(74) Attorney, Agent, or Firm—Wolf, Greenfield & Sacks, P.C.

(57) ABSTRACT

Chiral peptide nucleic acids are provided which hybridise strongly with complementary nucleic acids and have potential as antigene and antisense agents and as tools in molecular biology. The compounds have the formulae.

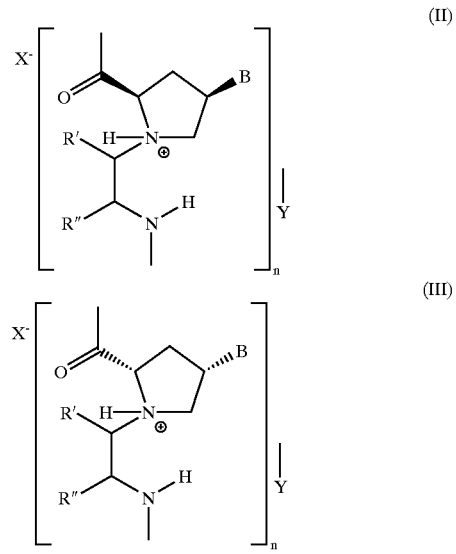

where
n is 1 to 200,
B is a protected or unprotected base,
X may be OH,
Y may be H, and R' and R", which are the same or different, are H, C1–C6 alkyl, aryl or aralkyl or R' or R", together the carbon atoms to which they are attached, form a cycloalkyl ring and protected derivatives thereof.

10 Claims, 4 Drawing Sheets

CHIRAL PEPTIDE NUCLEIC ACIDS WITH A N-AMINOETHYL-D-PROLINE BACKBONE

INTRODUCTION

This invention relates to novel chiral peptide nucleic acids (cPNAs) which hybridise strongly with complementary nucleic acids. As such they have potential as antigene and antisense agents and as tools in molecular biology.

DESCRIPTION OF RELATED ART

In our WO 98/16550 we describe PNAs of the formula:

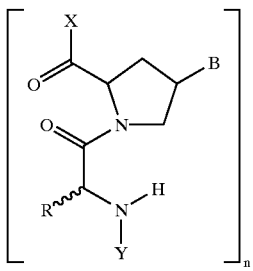

where n is 1 or 2–200

B is a protected or unprotected heterocyclic base capable of Watson-Crick or of Hoogsteen pairing.

R is H, C1–C12 alkyl, C6–C12 aralkyl or C6–C12 heteroaryl which may carry one or more substituents preferably selected from hydroxyl, carboxyl, amine, amide, thiol, thioether or phenol, X is OH or OR''' where R''' is a protecting group or an activating group or a lipophilic group or an amino acid or amino amide or nucleoside, Y is H or a protecting group or a lipophilic group or an amino acyl group or nucleoside.

When n is 1, these compounds are peptide nucleotide analogues. When n is 2 to about 30 these compounds are peptide oligonucleotides and can be hybridised to ordinary oligo or polynucleotides. Typically the two strands are hybridised to one another in a 1:1 molar ratio by base-specific Watson-Crick base pairing.

These chiral PNAs were shown to interact strongly with complementary DNA or RNA. Such chiral PNAs and their hybrids with oligonucleotides, however, have poor solubility in aqueous media, making biological studies difficult. Attempts to improve the solubility of PNAs have so far met with variable success.

BRIEF SUMMARY OF THE INVENTION

According to the present invention, there is provided a compound of formula (I):

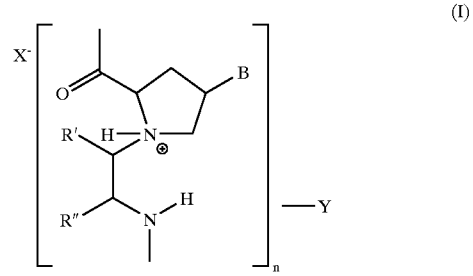

where n is 1 to 200,

B is a protected or unprotected base capable of Watson-Crick or of Hoogsteen pairing, X is OH or OR''' where R''' is a protecting group or an activating group or a lipophilic group or an amino acid or amino amide or nucleoside, Y is H or a protecting group or a lipophilic group or an amino acyl group or nucleoside and R' and R'' which are the same or different, are H, $C_{1-6}$ alkyl, aryl, ar(C1–C6)alkyl or R' and R'' together with the carbon atoms to which they are attached form a cycloalkyl ring.

B is a base capable of Watson-Crick or of Hoogsteen pairing. This may be a naturally occurring nucleobase selected from A, C, G, T and U; or a base analogue that may be base specific or degenerate, e.g. by having the ability to base pair with both pyrimidines (T/C) or both purines (A/G) or universal, by forming base pairs with each of the natural bases without discrimination. Many such base analogues are known e.g. hypoxanthene, 3-nitropyrrole, 5-nitroindole, and those cited in Nucleic Acids Research, 1989, 17, 10373–83 and all are envisaged for use in the present invention.

DETAILED DESCRIPTION OF THE INVENTION

The compounds of formula (I) contain proline of undefined stereochemistry. Although compounds with the trans-stereochemistry may have interesting properties, compounds with the cis-stereochemistry are preferred either with the D-configuration as shown in (II) or the L-configuration shown in structure (III).

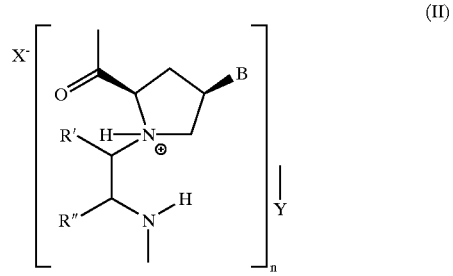

-continued

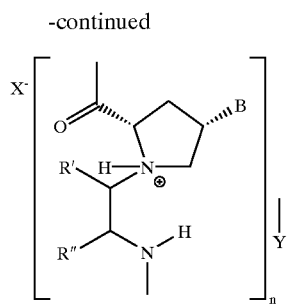

(III)

A particular compound is (IIa) of the formula:

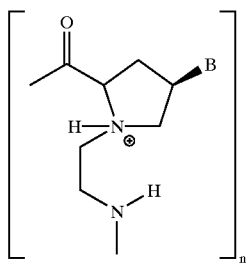

(IIa)

Any one of B, X and Y may include a signal moiety, which may be for example a radioisotope, an isotope detectable by mass spectrometry or NMR, a hapten, a fluorescent group or a component of a chemiluminescent or fluorescent or chromogenic enzyme system. The signal moiety may be joined to the peptide nucleotide analogue either directly or through a linker chain of up to 30 atoms as well known in the field.

R' and R" are preferably both hydrogen. Suitable alkyl groups which these groups may contain include methyl, ethyl, propyl and butyl and while suitable aryl groups include phenyl so that they may be, for example, benzyl. The cycloalkyl ring which can be formed is suitably cyclopentyl or cyclohexyl. These various groups can be substituted but the presence of heteroatoms is to be avoided as they tend to make the compound unstable. Replacing the glycine carbonyl group in the glycyl-proline backbone of cPNA with a methylene group ("aminoethylprolyl cPNA") creates a more conformationally flexible backbone while the conformation of the side chain is still restricted. Increasing conformational flexibility of the backbone might decrease the binding affinity due to the increased entropy loss upon hybridization, but it should allow the cPNA to adopt a wider range of conformations than the glycine-derived cPNAs. Combination of the two factors may decrease or increase the binding affinity of the resulting cPNA to its complementary oligonucleotide, depending on how close the conformation of the cPNA in the hybrid is to that in its native state. The basic proline-nitrogen atom should be at least partially protonated under physiological conditions and should attract the negatively charged phosphate group of DNA so providing further stabilization of the hybrid formed with natural DNA.

The present invention also provides a process for preparing the compounds of the present invention which comprises:

(i) de-protecting the heterocyclic amino group of a compound of the formula:

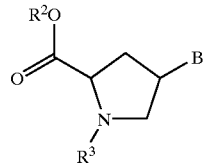

where
R$^2$ is a protecting group, for example Dpm (diphenylmethyl),
R$^3$ is a protecting group compatible with R$^2$ for example Boc (t-butoxycarbonyl), and
B is a protected or unprotected heterocyclic base capable of Watson-Crick or Hoogsteen pairing, in particular N$_3$-protected (such as by benzoyl) thymine, N$_6$-protected adenine, N$_4$-protected cytosine, N$_2$—O$_6$-protected guanine or N$_3$-protected uracil.

(ii) reacting the de-protected product of (i) with an N-protected aziridine, for example as N-p-nitro benzene sulphonyl aziridine, to provide a compound of the formula:

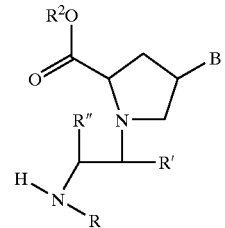

where R is a protecting group and optionally (iii) converting said R group to a different protecting group such as Boc or Fmoc (9-fluorenylmethyl formate) and optionally removing said protecting groups.

In another aspect the invention provides a method of converting a peptide nucleotide analogue of formula (I) in which n is 1 into a peptide oligonucleotide of formula (I) in which n is 2–200, comprising the steps of:

(i) providing a support carrying primary amine groups,
(ii) coupling an N-protected peptide nucleotide analogue of formula (I) to the support,
(iii) removing the N-terminal protecting group,
(iv) coupling an N-protected nucleotide analogue of formula (I) to the thus-derivatised support,
(v) repeating steps (iii) and (iv) one or more times, and
(vi) optionally removing the resulting peptide oligonucleotide from the support.

A synthetic route towards the N-aminoethylproline synthon carrying suitable protecting groups (7a and 7b) for solid phase peptide synthesis was developed (see scheme 1) (i) 2.5 equiv pTsOH/MeCN; (ii) N-nosylaziridine/DIEA/MeCN, rt; (iii) Boc$_2$O/Et$_3$N/DMAP in CH$_2$Cl$_2$; (iv) PhSH/K$_2$CO$_3$ in DMF, rt; (v) cyclohexane, cat Pd/C in MeOH, reflux; (vi) FmocCl/DIEA; (vii) 4 M HCl/dioxane. N-p-Nitrobenzenesulfonyl ("Nosyl") aziridine, obtained by treatment of N-nosylethanolamine with Ph$_3$P/DEAD in THF at low temperature, was employed as the electrophilic N-aminoethylating agent. The Boc group of protected cis- 4-thyminyl-D-proline (4) (synthesized previously) was selectively removed in the presence of diphenylmethyl (Dpm) ester using p-toluenesulfonic acid in acetonitrile under conditions previously reported. Nucleophilic ring opening of N-nosylaziridine by this free amine proceeded efficiently to give the desired N-aminoethylproline derivative (5). Reaction of (5) with $Boc_2O$ was achieved in the presence of 4-dimethylaminopyridine (DMAP) to give the N-Boc derivative. Treatment with thiophenol in the presence of potassium carbonate in DMF at room temperature gave the N-Boc derivative (6a) as an amorphous solid [50% yield from (4)]. Deprotection of the carboxyl group by catalytic transfer hydrogenolysis (cyclohexene, Pd-C) gave the free N-Boc amino acid (7a) in quantitative yield.

The Boc protecting group in (6a) was converted to the Fmoc group in order to take advantage of the milder conditions of peptide synthesis employing Fmoc protection strategy. When (6a) was treated with p-toluenesulfonic acid in acetonitrile followed by 9-fluorenylmethyl chloroformate (Fmoc-Cl) in the presence of DIEA, the Fmoc derivative (6b) was obtained in 80% yield. The carboxyl protecting group was removed by HCl/dioxane to give the free acid (7b) (71%) as its hydrochloride salt with the $N^3$-benzoyl protecting-group of thymine intact. The Fmoc protected monomer (7b) was oligomerized on Novasyn TGR resin, previously loaded with Fmoc-Lys(Boc) on 5 μmol scale using standard HBTU/DIEA activation protocol with capping at the end of each cycle. Quantitative monitoring of the coupling efficiency, by measurement of the absorbance of dibenzofulvene-piperidine adduct at 264 nm, after deprotection cycle revealed the average coupling yield of approximately 92%. Using the Fmoc-ON purification strategy, it was possible to isolate the Fmoc-(3a) together with its partially debenzoylated product without difficulty using reverse phase HPLC. Subsequent treatment with 20% aqueous piperidine followed by HPLC gave the fully deprotected (3a).

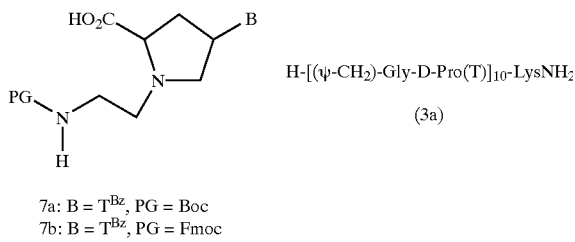

H-[(ψ-$CH_2$)-Gly-D-Pro(T)]$_{10}$-LysNH$_2$ (3a)

7a: B = $T^{Bz}$, PG = Boc
7b: B = $T^{Bz}$, PG = Fmoc

ESI mass spectrometric analysis revealed a single peak corresponding to the expected product ($M_r$=2787.27, calcd for $M_r$=2788.06). In contrast to the analogous glycylproline PNA with the same $T_{10}$ sequence, the product is freely soluble in aqueous solvents and a concentration exceeding 5 mg/mL could be achieved (Scheme 1).

Scheme 1

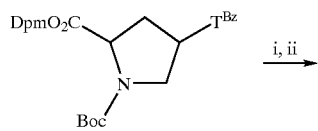

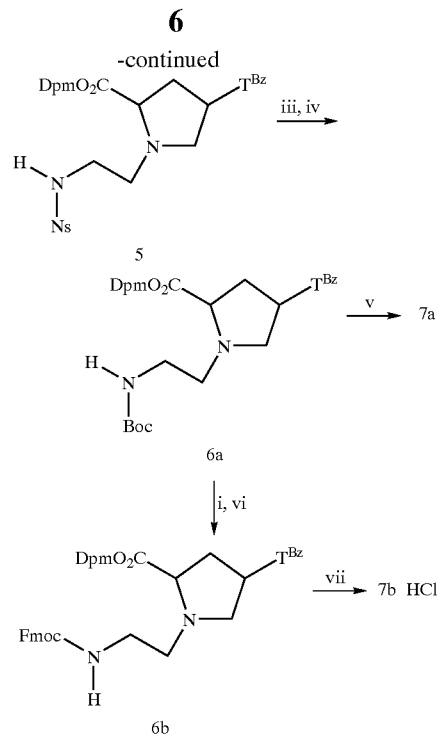

BRIEF DESCRIPTION OF THE DRAWINGS

FIG. 3 gives a reverse phrase HPLC trace.

Figure 1:
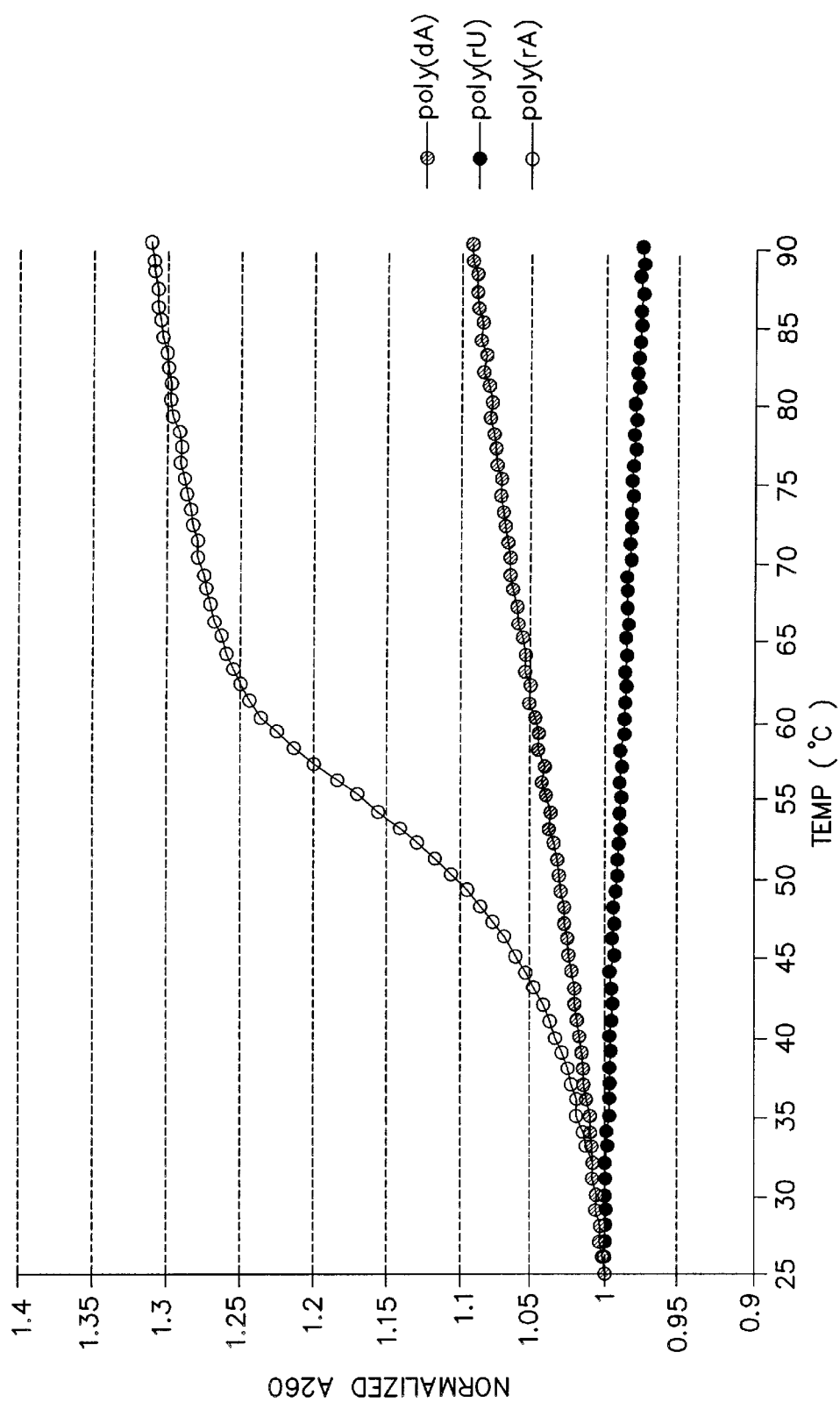
FIG. 1 is a melting point curve for compound (3a) and poly (rA), (sigmoid curve with inflection at 53° C.) poly (rU) (rising straight line plot) and poly (dA) (falling straight line plot) Conditions: 10 mM sodium phosphate buffer pH 7.0; 150 mM NaCl; 1.0 μM (3a); ratio of T:A=1:1, 20% hypochromicity.

Interaction between the decathymine PNA oligomer (3a) with poly(rA), poly(dA), and (dA)$_{10}$ was investigated by $T_m$ measurement. Melting was observed when the nucleic acid component is poly(rA) with a single transition at $T_m \cong 53°$ C. (150 mM NaCl). A typical melting curve is shown in FIG. 1 and the $T_m$ values are as shown in Table 1 and the $T_m$ values are shown in Table 1. Control experiments with poly(rU) and poly(rI) showed no observable melting curve, suggesting that the interaction is specific for A·T base pairing. UV titration between (3a) and poly(rA) revealed a 2:1 stoichiometry of T:A, indicating the formation of a triple helical complex, probably via Watson-Crick and Hoogsteen-type T·A·T pairing similar to those observed with other homopyrimidine PNAs.

Figure 2A:
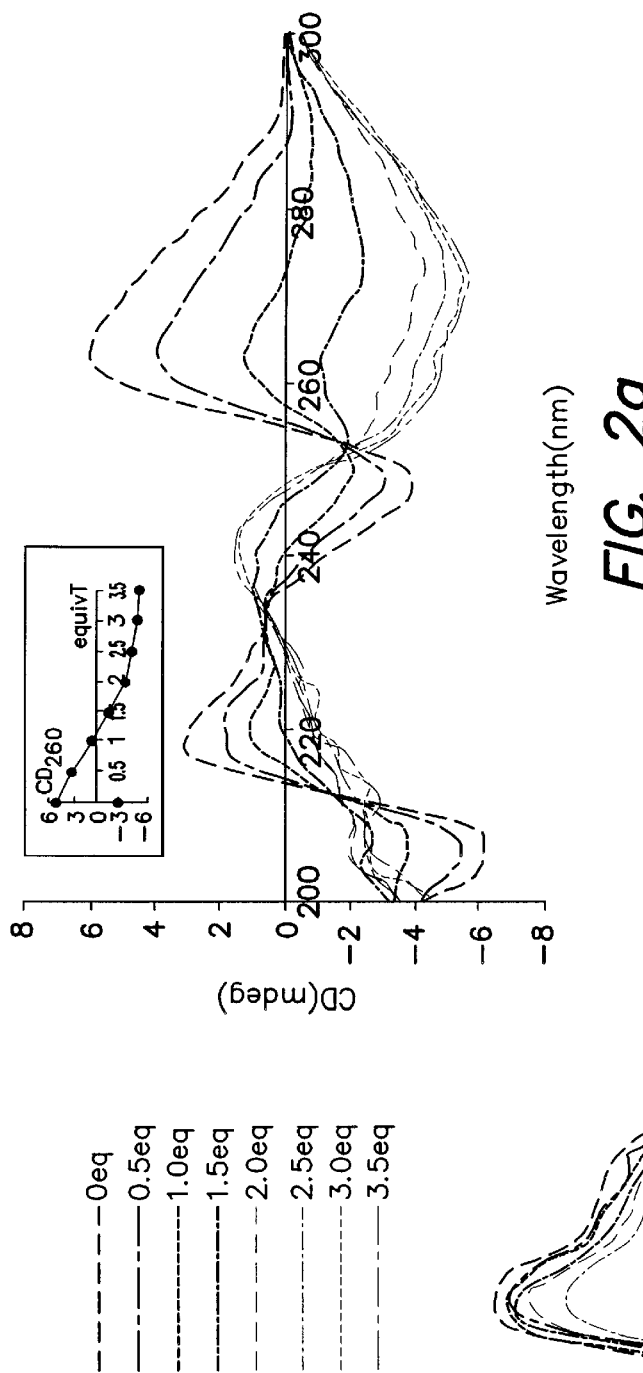
FIG. 2A is a CD spectra of mixture of poly(rA) and (3a) at different equivalents of T; inset: plot of $\epsilon_{260}$ versus equivalents of T.
Figure 2B:
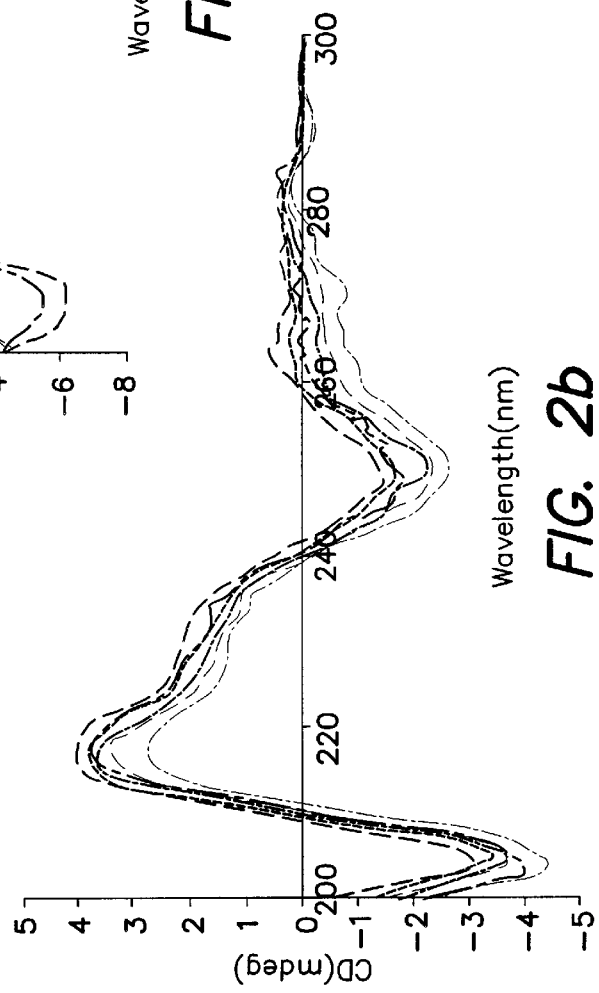
FIG. 2B is a CD spectra of mixture of poly(dA) and (3a) at different equivalents of T. Conditions 10 mM sodium phosphate buffer pH 7.0. The concentration of poly (rA) and poly (dA) was 10 μM based on AMP.

The interaction of cPNA and poly(A) was further studied by CD spectroscopy. While single stranded poly(rA) exhibited a characteristic CD signal in the region of 200–300 nm, single-stranded cPNA (3a) exhibited very weak CD spectra in this region. Any change in CD signal of the mixture between (3a) and poly(rA) would therefore indicate the formation of new species. As expected, addition of (3a) to poly(rA) resulted in a strong induced CD signal with a minima at 275 nm (FIG. 2a) whereas no significant change was observed when (3a) was added to poly(dA) under the same conditions (FIG. 2b). The shape of the CD curve is, however, significantly different from those of conventional DNA-DNA and DNA-RNA complexes thus possibly indicating a new type of helical structure. By following the CD signal as a function of amount of (3a) added, the stoichiometry of binding of PNA:RNA was found to be 2:1, consistent with the result obtained from UV titration. Gel electrophoresis experiments between (3a) and fluorescent labelled $(dA)_{10}$ also confirmed the lack of binding between (3a) and $(dA)_{10}$.

TABLE 1

Comparison of $\tau_m$ of hybrids between PNA and oligonucleotides[a]

| Hybrids | $T_m$ (° C.) | Stoichiometry (PNA, DNA/RNA) |
|---|---|---|
| (1a):poly(dA) | 73 | 2:1 |
| (2a):poly(dA) | 70 | t 1 |
| (3a):poly(dA) | —[b] | — |
| (3a):poly(rA) | 53 | 2:t |
| (3a):poly(rU) | —[b] | — |
| (3a):poly(rt) | —[b] | — |

(1a) H-[Acg(T)]$_{10}$-LysNH$_3$ (1b): H-[Gly-o-Pro(cis-τ)]$_{10}$-LysNH,
[a]Conditions. see FIG. 1.
[b]No melting above 20° C. was observed Although the hybrid between PNA oligomer (3a) and poly(rA) exhibited lower $T_m$ value compared to Nielsen's type PNA (1a) or glycylproline cPNA (2a) the $T_m$ is still remarkably high compared to the natural oligodeoxyribonucleotide $(dT)_{10}$ ($T_m<20°$ C. under comparable conditions). The lowered $T_m$ compared to the glycylproline cPNA emphasises the importance of restricting the conformation. The electrostatic interaction between the protonated form of the proline nitrogen atom and the negatively charged phosphate group of the nucleic acid may be a factor that provides a positive contribution to the binding. This is supported by the fact that no binding of (3a) to poly(rA) could be observed at high salt concentration (1.0 M NaCl). The selective recognition of polyribonucleotide in preference to polydeoxyribonucleotide is, however, of great interest with regard to its use in antisense research. Furthermore, the results are in sharp contrast to recent work on related aminoethylproline PNA systems but with different stereochemistry around the proline ring [i.e. (2S, 4S) and 2R, 4S)], in which both stereoisomers were reported to bind strongly with complementary oligodeoxyribonucleotides according to $T_m$ studies.

Thus the compounds carrying a hydrophilic N-aminoethylproline backbone can be readily synthesised used standard peptide chemistry. The cPNA is readily soluble in aqueous solvents and exhibit strong interaction with oligoribonucleotides but not with oligodeoxyribonucleotides. Such high selectivity suggests it has potential as an antisense agent where selective targeting of mRNA would be beneficial.

Accordingly the present invention also provides a pharmaceutical composition which comprises a compound of the present invention and a pharmaceutically acceptable diluent or carrier.

The following Example further illustrates the present invention:

EXAMPLE 1

General

Melting points were recorded on a Kofler block apparatus and are quoted uncorrected. Specific rotations were measured on a Perkin-Elmer 241 polarimeter. IR spectra were recorded on a Perkin-Elmer 1750 or Nicolet Impact 410 Fourier Transform Infrared spectrometer. Elemental analyses were performed on a Perkin-Elmer CHN analyser model PE2400 series II.

Routine $^1$H and $^{13}$C nmr spectra were recorded on a Varian Gemini 200 spectrometer or Bruker ACP 200 operating at 200 MHz ($^1$H) and 50.28 MHz ($^{13}$C). $^{13}$C spectra were recorded in broad band decoupled mode and the chemical shift assignment was assisted by a DEPT experiment. High field nmr experiments were performed on either Bruker DRX400 (400 MHz) or Bruker AMX 500 spectrometer (500 MHz). $^1$H and $^{13}$C chemical shifts are quoted in ppm relative to tetramethylsilane and were internally referenced to the residual protonated solvent signal.

Chemical ionisation and fast atom bombardment mass spectra were recorded on a VG 20-250 Masslab and a VG Micromass ZAB-1F mass spectrometer. Electrospray mass spectra were recorded on a VG Biotech BioQ or VG Biotech Platform. Masses are quoted as m/z unless otherwise stated, only the molecular ions and major fragments being quoted.

Thin layer chromatography was performed on Merck D.C.-Alufolien Kieselgel 60 $F_{254}$ 0.2 mm pre-coated aluminium plates. Flash column chromatography was carried out on Janssen Chimica C60 silica gel (35–70μ particle size).

Distilled water was used for all chemical experiments. Chemicals and solvents were obtained from Fluka AG or Aldrich Chemical Company Ltd and were purified if necessary according to the literature. N-Boc-trans-4-hydroxy-D-proline diphenylmethyl ester was synthesized as described previously. DMF was peptide synthesis grade obtained from Rathburn Chemical Ltd. and was used without further purification except when strictly anhydrous conditions were required where it was redistilled from calcium hydride under reduced pressure. Acetonitrile was hplc grade obtained from Rathburn and used without further purification.

Peptide Synthesis—General

The solid support for peptide synthesis, Novasyn™ TGR resin (~0.20–0.25 mmol free NH$_2$ group/g) and Fmoc-Lys (Boc)-OPfp were obtained from Calbiochem-Novabiochem Ltd. Trifluoroacetic acid (98%) was obtained from Avocado Research Chemicals Ltd and Fluka AG. All other reagents were obtained at highest purity grade available either from Aldrich Chemical Company Ltd. or Fluka A.G. and were used as received.

DMF was peptide synthesis grade obtained from Rathburn Chemicals Ltd. and used without further purification. All other solvents used for the synthesis and purification were hplc grade solvents obtained from Rathburn. Deionized water was obtained from an Elga Maxima Ultra-Pure water purification system.

Samples for reverse phase hplc analysis were dissolved in a suitable aqueous solvent and filtered through a teflon filter (0.47μ pore size, Anachem Ltd.). Hplc was performed on a Waters 990+ system with a diode array detector. A Waters μBondapak C-18 semi-preparative reverse phase hplc column (0.78×30 cm, P/N 84176) or Hypersil ODS 100×4.6 mm, 5μ particle size was used for both analysis and preparative purposes. Peak monitoring and data analysis were performed on Waters 990 software running on a NEC IBM-PC/AT compatible computer with 80286/80287 microprocessors. The samples were recovered from hplc fractions by freeze drying on a VirTis Freezemobile 5SL freeze drier. Electrospray mass spectra of the cPNA were recorded on a VG Biotech-BioQ or VG Biotech Platform mass spectrometers.

Routine UV measurement was performed on a Pye Unicam SP8-100 UV spectrophotometer. For more accurate work such as melting temperature measurement, the measurements were carried out on a Varian CARY 13 UV spectrophotometer equipped with a temperature control system. The machine was controlled by a CARY 13 software running on an IBM PS/2 system model 30/286.

N-(2-hydroxyethyl)-4-nitrobenzenesulfonamide

To a solution of ethanolamine (0.68 g, 11 mmol) and triethylamine (1.10 g, 10.9 mmol) in dichloromethane (20 mL) was added 4-nitrobenzenesulfonyl chloride (2.20 g, 9.9 mmol) portionwise with stirring. The resulting clear yellow solution was stirred at room temperature for 15 min. The clear yellow solution was diluted with equal volume of EtOAc and washed with water and then with 5% HCl. The organic phase was evaporated to dryness to give 1.36 g of light yellow crystalline solid which was dried and used without further purification. $\delta_H$ (200 MHz, DMSO-$d_6$) 2.90 [2H, m, NHC$\underline{H}_2$CH$_2$OH], 3.36 [2H, m, NHCH$_2$C$\underline{H}_2$OH], 4.75 [1H, t, O$\underline{H}$], 8.00 [1H, m, N$\underline{H}$], 8.02 and 8.38 [2×2H, q ($A_2B_2$), 2×Nosyl C$\underline{H}$].

N-Nitrobenzenesulfonylaziridine

A suspension of N-(2-hydroxyethyl)-nitrobenzenesulfonamide (1.50 g, 6.1 mmol) and triphenylphosphine (1.65 g, 6.29 mmol) in THF (20 mL) was treated with diethyl azodicarboxylate (1.20 mL, 7.72 mmol) dropwise at 0° C. After stirring at 0° C. for 15 min, a yellow crystalline precipitate began to form. Tlc analysis indicated complete reaction at this point. The solvent was evaporated to dryness and the residue purified by column chromatography (SiO$_2$, dichloromethane) to give the aziridine as yellow crystalline solid (0.826 g, 59%) $\delta_H$ (200 MHz; CDCl$_3$) 2.45 [4H, s, 2×aziridine C$\underline{H}_2$], 8.06 and 8.40 [2×2H, q ($A_2B_2$) 2×Nosyl C$\underline{H}$].

N-(2-Nitrobenzenesulfonamidoethyl)-cis-4-($N^3$-benzoylthymin-1-yl)-D-proline diphenylmethyl ester (5)

Boc-D-Pro(cis-$T^{Bz}$)-ODpm (4) (1.20 g, 1.97 mmol) was dissolved in acetonitrile (5 mL). p-Toluenesulfonic acid monohydrate (900 mg, 4.73 mmol) was added and the solution was stirred at room temperature for 2 h, after which tlc indicated complete deprotection of the N-Boc group. Diisopropylethylamine (1.50 mL, excess) and N-nosylaziridine (430 mg, 2.0 mmol) were added with stirring and the reaction mixture was stirred at room temperature overnight. It was then diluted with dichloromethane (50 mL) followed by washing with water. The organic phase was dried (MgSO$_4$) and the solvent removed under reduced pressure to give the crude product as an oil which was purified by column chromatography (SiO$_2$, EtOAc:Hexane 1:1→2:1). The product was obtained as a white foam (0.831 g, 57%), $\delta_H$ (200 MHz; CDCl$_3$) 1.90 [3H, s, thymine C$\underline{H}_3$], 1.95 [1H, m, 1×C$\underline{H}_2$(3')], 2.60–3.30 [7H, m, 1×C$\underline{H}_2$(3'), CH$_2$(5') and 2×aminoethyl C$\underline{H}_2$], 3.45 [1H, dd, C$\underline{H}$(2')], 5.20 [1H, m, C$\underline{H}$(4')], 6.00 [1H, br m, N$\underline{H}$], 6.85 [1H, s, C$\underline{H}$Ph$_2$], 7.30 [10H, m, Dpm aromatic CH], 7.46 [2H, t, Bz m-C$\underline{H}$], 7.62 [1H, t, Bz p-C$\underline{H}$], 7.78 [1H, s, thymine C(6)$\underline{H}$], 7.90 [2H, d, Bz o-C$\underline{H}$], 8.00 and 8.20 [2×2H, q ($A_2B_2$), 2×Nosyl C$\underline{H}$]; $\delta_C$ (50.28 MHz; CDCl$_3$) 12.7 [thymine $\underline{C}$H$_3$], 36.8 [$\underline{C}$H$_2$(3')], 41.5 [NsNH$\underline{CH}_2$CH$_2$N], 52.5 and 52.8 [$\underline{C}$H$_2$(5') and $\underline{C}$H(4')], 58.0 [$\underline{C}$H(2')], 64.5 [NsNH$\underline{CH}_2$CH$_2$N], 79.6 [$\underline{C}$HPh$_2$], 112.5 [$\underline{C}$(5)], 124.0–131.9 [aromatic $\underline{C}$H], 135.2 and 138.0 [$\underline{C}$(6)H and benzoyl p-$\underline{C}$H], 139.2 [Benzoyl $\underline{C}$], 146.1 [Nosyl aromatic $\underline{C}$], 150.3 [$\underline{C}$(2)], 162.8 [$\underline{C}$(4)], 169.5 [benzoyl $\underline{C}$O], 173.0 [ester $\underline{C}$O], m/z (APCI+) 761 (M+Na$^+$, 23%), 738 (M+H$^+$, 86), 266 (13.5), 167 (Ph$_2$CH$^+$, 100); $[\alpha]_D^{23}$ +22.9 (c=1.04, CHCl$_3$)

N-2-(N-tert-Butoxycarbonylamino)ethyl-cis-4-($N^3$-benzoylthymin-1-yl)-D-proline diphenylmethyl ester (6a)

A solution of N-(2-Nitrobenzenesulfonamidoethyl)-cis-4-(benzoylthymin-1-yl)-D-proline diphenylmethyl ester (5) (1.20 g, 0.46 mmol) was dissolved in dichloromethane (5 mL). Boc$_2$O (110 mg, 0.50 mmol) and triethylamine (5 mL) was added with stirring followed by 4-dimethylaminopyridine (10 mg, cat.). The yellow solution was stirred at room temperature for 6.5 h then evaporated to dryness to give N-2-(N'-4-Nitrobenzenesulfonyl-N'-tert-butoxycarbonyl)aminoethyl)-cis-4-(benzoylthymin-1-yl)-D-proline as yellow foam. Treatment of this material (max 0.46 mmol) with anhydrous K$_2$CO$_3$ (85 mg, 0.60 mmol) and thiophenol (66 mg, 0.60 mmol) in DMF (2 mL) at room temperature afforded an orange-yellow solution. The reaction mixture was then diluted with dichloromethane, washed with water and evaporated to dryness. The resulting yellow oil was purified by column chromatography (SiO$_2$; EtOAc:Light Petroleum 1:1→2:1) to give the product as white foam 186.3 mg (62%, 2 steps); $\delta_H$ (200 MHz; CDCl$_3$) 1.46 [9H, s, $^t$Bu C$\underline{H}_3$], 1.90 [3H, s, thymine C$\underline{H}_3$], 1.95 and 2.60 [2H, 2×m, C$\underline{H}_2$(3')], 2.70–3.30 [6H, m, C$\underline{H}_2$(5') and 2×aminoethyl C$\underline{H}_2$], 3.42 [1H, dd, C$\underline{H}$(2')], 5.12 [1H, m, C$\underline{H}$(4')], 5.28 [1H, br m, N$\underline{H}$], 6.98 [1H, s, C$\underline{H}$Ph$_2$], 7.36 [10H, m, Dpm aromatic C$\underline{H}$], 7.50 [2H, t, Bz m-C$\underline{H}$], 7.63 [1H, t, Bz p-C$\underline{H}$], 7.90 [2H, d, Bz o-C$\underline{H}$] and 7.98 [1H, s, thymine C(6)$\underline{H}$]; m/z (APCI+) 676 (M+Na$^+$, 18.5%), 653 (M+H$^+$, 59), 597 (M−C$_4$H$_8^+$, 25), 554 (M−Boc$^+$, 9), 475 (26.5), 167 (Ph$_2$CH$^+$, 100); $[\alpha]_D^{22}$ +6.5 (c=1.06, CHCl$_3$)

N-2-(N-tert-Butoxycarbonylamino)ethyl-cis-4-($N^3$-benzoylthymin-1-yl)-D-proline (7a)

N-2-(N-tert-Butoxycarbonylamino)ethyl-cis-4-($N^3$-benzoylthymin-1-yl)-D-proline diphenylmethyl ester (6a) (150 mg, 0.23 mmol ) was heated at reflux with cyclohexene (1.0 mL) and methanol (10 mL) in the presence of 10% Pd/C (100 mg) for 5 h. The catalyst was removed by filtration through Celite, the filtrate evaporated to dryness and the residue re-precipitated from EtOAc-light petroleum to give a white solid (80.2 mg, 72%) $\delta_H$ (200 MHz; CDCl$_3$) 1.42 [9H, s, $^t$Bu C$\underline{H}_3$], 1.95 [3H, s, thymine C$\underline{H}_3$], 2.05 [1H, m, 1×C$\underline{H}_2$(3')], 2.60–3.50 [m, C$\underline{H}_2$(5') and 2×aminoethyl C$\underline{H}_2$ and C$\underline{H}$(2')], 4.65 [1H, br m, O$\underline{H}$?], 5.18 [1H, m, C$\underline{H}$(4')], 5.60 [1H, br m, N$\underline{H}$]; 7.36 [10H, m, Dpm aromatic C$\underline{H}$], 7.48 [2H, t, Bz m-C$\underline{H}$], 7.60 [1H, t, Bz p-C$\underline{H}$], 7.89 [2H, d, Bz o-C$\underline{H}$], 8.01 [1H, s, thymine C(6)$\underline{H}$]; m/z (APCI+) 509 (M+Na$^+$, 38%), 487 (M+H$^+$, 56), 431 (M−C$_4$H$_8^+$, 45), 309 (100), 155 (82); $[\alpha]_D^{23}$ +12.2 (c=1.04, CHCl$_3$)

N-2-(9-Fluorenylmethoxycarbonylamino)ethyl-cis-4-($N^3$-benzoylthymin-1-yl)-D-proline diphenylmethyl ester (6b)

N-2-(N-tert-Butoxycarbonylamino)ethyl-cis-4-($N^3$-benzoylthymin-1-yl)-D-proline diphenylmethyl ester (6a) (550 mg, 0.84 mmol) was dissolved in acetonitrile (5 mL). p-Toluenesulfonic acid monohydrate (380 mg, 2.00 mmol) was added and the solution was stirred at room temperature for 4 h (another 380 mg portion of p-Toluenesulfonic acid monohydrate was added after 1 h), after which tlc indicated complete deprotection of the N-Boc group Diisopropylethylamine (850 μL, 5 mmol) and 9-fluorenylmethylchloroformate (283 mg, 1.10 mmol) were added with stirring and the reaction mixture was stirred at room temperature for 1 h. It was then diluted with dichloromethane (50 mL) followed by washing with water. The organic phase was dried (MgSO$_4$) and the solvent removed under reduced pressure. The residue was purified by column chromatography (SiO$_2$; EtOAc:Hexane 1:1→2:1). The product was obtained as a white foam (520 mg 80%), m.p. 94–98° C., (Found C, 72.1; H, 5.49; N, 7.10%; C$_{47}$H$_{42}$N$_4$O$_7$+0.5H$_2$O requires C, 72.0; H, 5.53, N, 7.15%); $\delta_H$ (200 MHz; CDCl$_3$) 1.85 [3H, s, thymine C$\underline{H}_3$], 1.95 and 2.65 [2H, 2×m, C$\underline{H}_2$(3')], 2.70–3.40 [6H, m, C$\underline{H}_2$(5') and 2×aminoethyl C$\underline{H}_2$], 3.45 [1H, dd, C$\underline{H}$(2')], 4.25–4.55 [3H, m, Fmoc aliphatic C$\underline{H}$, C$\underline{H}_2$], 5.25 [1H, m, C$\underline{H}$(4')], 5.56 [1H, br m, N$\underline{H}$], 7.02 [1H, s, C$\underline{H}$Ph$_2$], 7.35 [10H, m, Dpm aromatic C$\underline{H}$], 7.40–8.00 [m, thymine C(6)$\underline{H}$, Fmoc aromatic C$\underline{H}$ and Bz C$\underline{H}$)]; $\delta_C$ (50.28 MHz; CDCl$_3$) 12.5 [thymine $\underline{C}$H$_3$], 36.5 [$\underline{C}$H$_2$(3')], 39.3 [FmocNH$\underline{C}$H$_2$CH$_2$N], 47.2 [Fmoc aliphatic $\underline{C}$H], 52.5 [$\underline{C}$H$_2$(5')], 53.2 [$\underline{C}$H(4')], 58.3 [$\underline{C}$H(2')], 65.0 [Fmoc $\underline{C}$H$_2$], 66.8 [FmocNH$\underline{C}$H$_2$CH$_2$N], 78.2 [$\underline{C}$HPh$_2$], 111.7 [$\underline{C}$(5)], 120.2 [Fmoc aromatic $\underline{C}$H], 125.0–131.8 [aromatic $\underline{C}$H], 135.2 and 137.8 [$\underline{C}$(6)H and benzoyl p-$\underline{C}$H], 139.5 and 139.6 [aromatic $\underline{C}$], 141.6 and 144.2 [Fmoc aromatic $\underline{C}$], 150.3 [$\underline{C}$(2)], 156.8 [Fmoc $\underline{C}$O], 163.0 [$\underline{C}$(4)], 169.5 [benzoyl $\underline{C}$O], 172.8 [ester $\underline{C}$O]; m/z (APCI+) 775 (M+H$^+$, 98%), 553 (18.5), 265 (21), 167 (Ph$_2$CH$^+$, 74); 137 (100); $\nu_{max}$(KBr)/cm$^{-1}$ 1746s, 1722s, 1697s and 1653s (C=O); [α]$_D^{23}$+7.03 (c=0.92, CHCl$_3$)

N-2-(9-Fluorenylmethoxycarbonylamino)ethyl-cis-4-(N$^3$-benzoylthymin-1-yl)-D-proline hydrochloride (7b)

N-2-(9-Fluorenylmethoxycarbonylamino)ethyl-cis-4-(benzoylthymin-1-yl)-D-proline diphenylmethyl ester (6b) 379.4 mg (0.49 mmol) was dissolved in 5 mL of 4 M HCl in dioxane and the solution left overnight. The volatiles were removed and the procedure repeated again (24 h). The residue was re-dissolved in dichloromethane and evaporated three times. Finally Et$_2$O was added to precipitate the product as white solids (223.8 mg, 71%) m.p. 144–146° C.; $\delta_H$ (200 MHz; DMSO-d$_6$+1 drop D$_2$O) 1.80 [3H, s, thymine C$\underline{H}_3$], 1.85 and 2.35 [2H, 2×m, C$\underline{H}_2$(3')], 2.80–3.95 [m, C$\underline{H}_2$(5') and 2×aminoethyl C$\underline{H}_2$ and C$\underline{H}$(2')], 4.15–4.35 [3H, m, Fmoc aliphatic C$\underline{H}$, C$\underline{H}_2$], 5.20 [1H, m, C$\underline{H}$(4')], 7.20–8.00 [m, thymine C(6)$\underline{H}$, Fmoc aromatic C$\underline{H}$ and Bz C$\underline{H}$]; m/z (APCI+) 631 (M+Na$^+$, 6%), 609 (M+H$^+$, 8), 333 (7), 265 (12), 179 (26), 137 (100); $\nu_{max}$ (KBr)/cm$^{-1}$ 1748s, 1733s, 1694s and 1645s (C=O); [α]$_D^{23}$ +13.5 (c=1.00, DMF).

General protocol for solid phase synthesis of cPNA (Fmoc chemistry)

Synthesis of cPNAs were carried out on 2.5 or 5.0 mmol scales on Novasyn TGR resin [0.20 mmol/g substitution, preloaded with Fmoc-Lys(Boc)-OH; 10–25 mg, ca. 2.5–5 µmol]. The synthesis cycle is as follows: deprotection: 20% piperidine in DMF (1.0 mL, 15 min), wash (DMF), coupling [Pfp ester/HOBt (1:1) or free acid/HBTU/DIEA (1:1:2) in DMF, 4 eq, 1 H], wash (DMF), capping (10% Ac$_2$O/lutidine in DMF), wash (DMF). The coupling reaction was monitored by measurement of the amounts of dibenzofulvene-piperidine adduct released upon deprotection at 264 and 297 nm. After addition of the final residue was completed, the N-terminal Fmoc group was either removed by 20% piperidine in DMF or retained as it was depending on the efficiency of the synthesis. The cPNA was released from the resin by treatment with 95% trifluoroacetic acid (ca. 1 mL for 10 mg resin) at room temperature for 2–3 h with occasional agitation. After the specified period of time, the cleavage solution was evaporated to nearly dryness by a stream of nitrogen then diluted with diethyl ether (ten times the volume). The suspension was then centrifuged at 13,000 rpm for 5 min. After decanting the supernatant, the crude PNA was washed with ether and the centrifugation-wash process repeated 2–3 times. Finally the crude PNA was air dried and dissolved in 10% aqueous acetonitrile containing 0.1% trifluoroacetic acid. The crude solution was filtered and analysed or purified by reverse phase hplc. The sample elution was carried out using a gradient of water-acetonitrile containing 0.1% trifluoroacetic acid (monitoring by UV absorbance at 270 nm).

General protocol for removal of Fmoc group from purified Fmoc-ON cPNA

Method A

To an aqueous solution of the Fmoc-ON PNA (50–100 µL) was added piperidine (10–20 µL) and the solution mixed by vortexing. After 20 min at room temperature or below, the solution was diluted with water (ca 1 mL) then freeze dried. The residue was dissolved in aqueous acetonitrile and purified by HPLC, which usually showed dibenzofulvene-piperidine adduct as the only contaminant.

Method B

To the freeze dried PNA (20–50 µg) was added 20% piperidine in DMF (20–50 µL) and the solution mixed by vortexing. After 20 min at room temperature, ether was then added. The precipitated peptide was isolated by centrifugation and washed a few times with ether and finally air dried. The residue was dissolved in aqueous acetonitrile and purified by reverse phase hplc.

H-[(ψ-CH$_2$)Gly-D-Pro(T)]$_{10}$-LysNH$_2$ yield: 42% (calculated from absorbance of the Fmoc chromophore relaeased at the final deprotection)

Figure 3A:
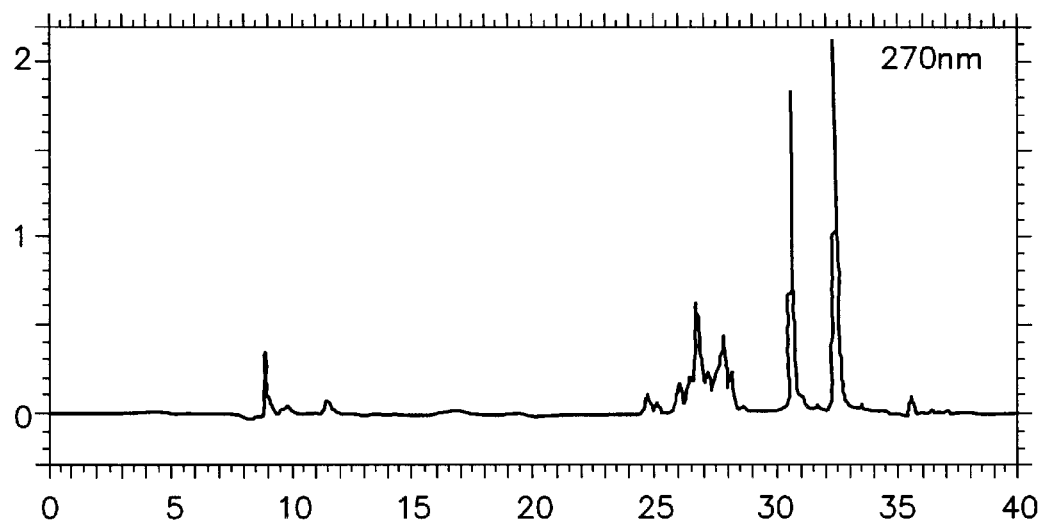
FIG. 3A hows crude Fmoc ON peptide nucleic acid (30.2 min=+Fmoc; 32.7 min=+Fmoc+Bz)
Figure 3B:
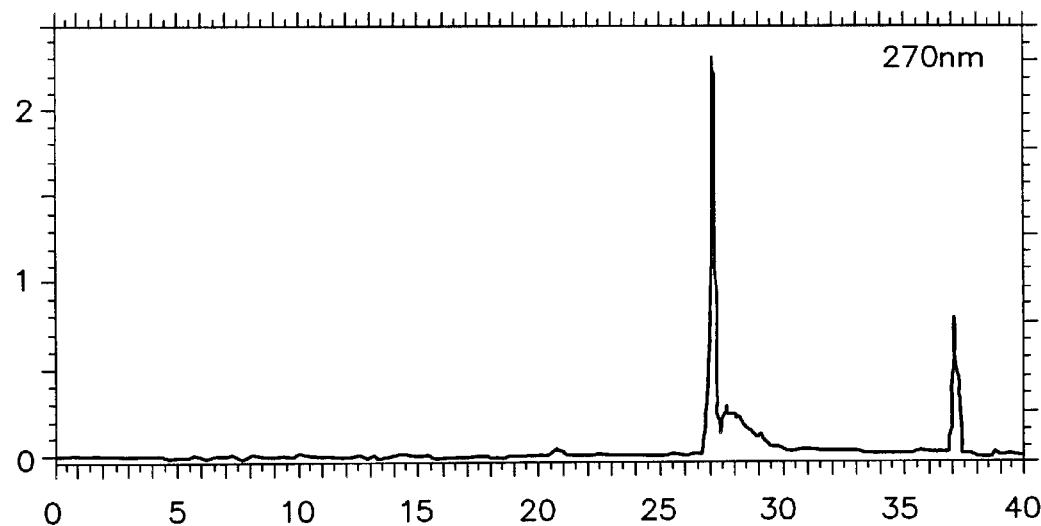
FIG. 3B shows purified Fmoc ON peptide nucleic acid after treatment with aqueous piperidine; HPLC conditions: column—Genesis C18 4.6×250 mm, 4μ particle size (Jones Chromatography); solvents—A=0.1% TFA in MeCN, B=0.1% aqueous TFA, 10:90 A:B for 5 min then linear gradient to 90:10 A:B over a period of 30 mins; flow rate 0.5 ml/min; detection wavelength 270 nm.
Figure 4:
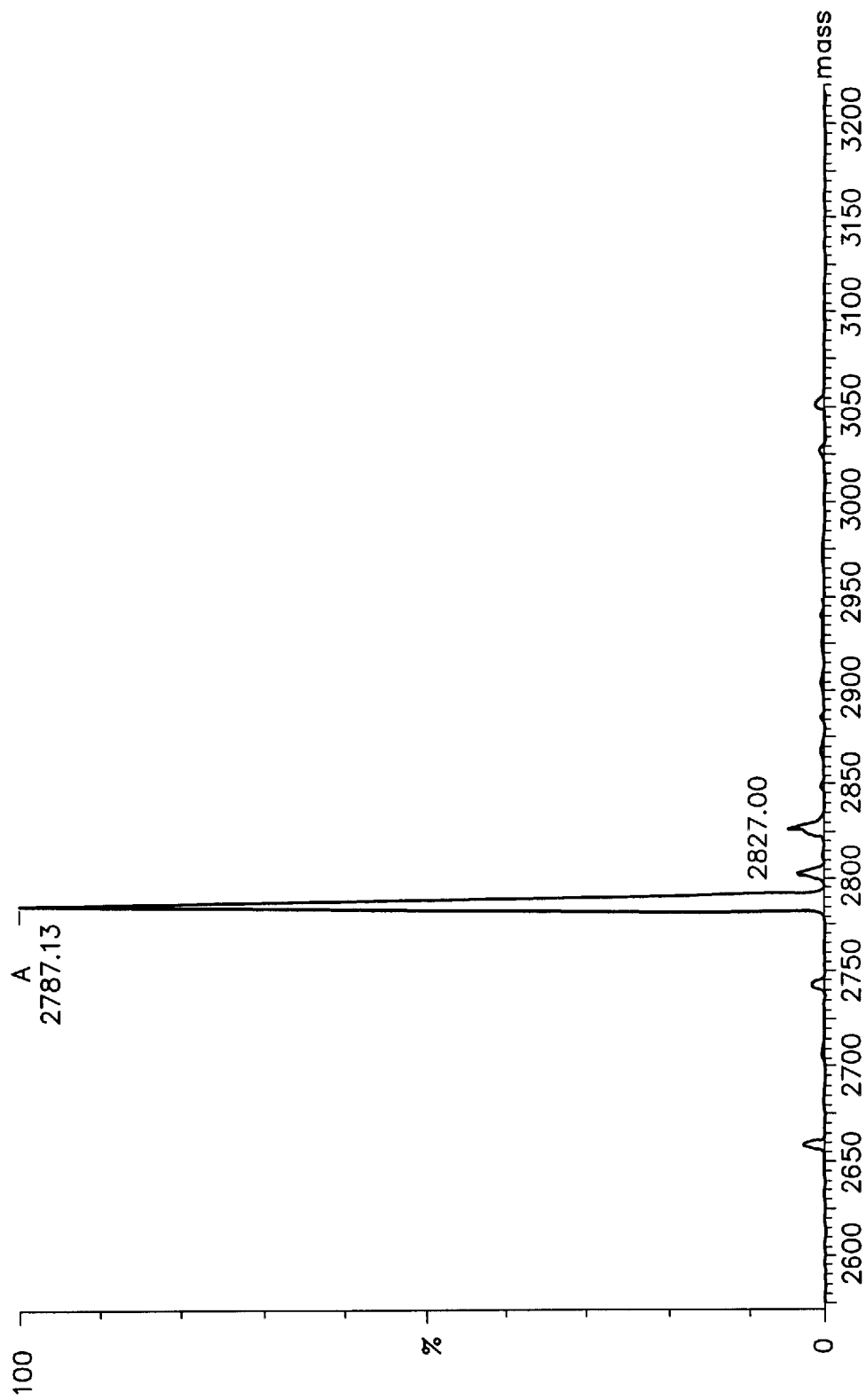
FIG. 4 is an electrospray mass spectrum (deconvoluted mass, Mr) of 3(a) (Mr found 2787.27; calcd for M=2788.06).

$t_R$=26.9 min (Fmoc-OFF); 30.2 min (Fmoc-ON); 32.7 (Fmoc/Bz)

hplc conditions:
  column—Genesis C18 4.6×250 mm, 4µ particle size (Jones Chromatography)
  solvents—A=0.1% TFA in MeCN, B≡0.1% aqueous TFA, 10:90 A:B for 5 min then linear gradient to 90:10 A:B over a period of 30 min. FIG. 3 gives the results. (a) crude Fmoc ON peptide nucleic acid (30.2 min=+Fmoc; 32.7 min++Fmoc+Bz) (b) purified Fmoc ON peptide nucleic acid after treatment with aqueous piperidine;

M$_r$ found 2787.27, calcd for M=2788.06. FIG. 4 gives the results.

Biophysical Studies—General

Poly(rA) (M$_r$~7×10$^6$) and poly(rU) (M$_r$<9×10$^5$) was obtained from Fluka AG. Poly(dA) (Mr~9.19×10$^5$) was obtained from Amersham Pharmacia Biotech. Poly(rI) was obtained from Sigma. The oligonucleotide, (dA)$_{10}$ and fluorescent labelled (dA)$_{10}$ was obtained in deprotected and hplc-purified form. All nucleic acids and oligonucleotides were used as received without further treatment.

The concentration of oligonucleotide, nucleic acid and cPNA solutions was determined from the absorbance at 260 nm (OD$_{260}$). The following molar extinction coefficients (ε) were used without compensation for the hypochromic effect due to the formation of ordered secondary structure of single-stranded nucleic acids: A, 15.4; T, 8.8; U, 9.9; I, 7.1 mL.µmol$^{-1}$.cm$^{-1}$. The same values were also used for cPNA.

T$_m$ experiments

T$_m$ experiments were performed on a CARY 100 UV Spectrophotometer (Varian Ltd.) equipped with a thermal melt system. The sample for T$_m$ measurement was prepared by mixing calculated amounts of stock oligonucleotide and cPNA solutions together to give final concentration of nucleotides and sodium phosphate buffer (pH 7.0) and the final volumes were adjusted to 3.0 mL by addition of deionized water. The samples were transferred to a 10 mm quartz cell with teflon stopper and equilibrated at the starting temperature for at least 30 min. The $OD_{260}$ was recorded in steps from 20–95° C. (block temperature) with a temperature increment of 0.5° C./min. The results were normalized by dividing the absorbance at each temperature by the initial absorbance. Analysis of the data was performed on a PC-compatible computer using Microsoft Excel 97 (Microsoft Corp.).

UV-Titration experiment

The UV titration experiment was performed on a CARY 100 UV Spectrophotometer (Varian Ltd.) at 20° C. To a solution containing the cPNA and 10 mM sodium phosphate buffer pH 7.0 (2.0 mL) was added a 1–5 μL aliquot of a concentrated stock solution of poly(rA) (concentration=100× as compared to the cPNA) in 10 mM sodium phosphate buffer pH 7.0. The absorbance was read against a blank (10 mM sodium phosphate) and more poly(rA) aliquots were added until a total volume of 40 μL had been added. The ratio of the observed $OD_{260}$ and the calculated $OD_{260}$ were plotted against the mole ratio of T:A nucleotide and the stoichiometry was determined from the inflection point (see Biochemistry, 1969, 8 3928).

Circular dichroism spectroscopy

All CD experiments were performed on a JASCO Model J-710/720 spectropolarimeter (Oxford Centre of Molecular Sciences, Oxford). The samples were prepared by mixing calculated amounts of stock oligonucleotide and cPNA solutions together in a 10 mm quartz cell and the final volumes were adjusted to 2.00 mL by addition of deionized water containing an appropriate amount of sodium phosphate buffer pH 7.0 to give the final AMP concentration of 5 mM and phosphate buffer of 10 mM. The spectra were measured at 20° C. from 300 to 200 nm and averaged 4 times then subtracted from a spectrum of pure water under the same conditions.

Gel electrophoresis experiments

The gel electrophoresis apparatus used was a SE6000 Vertical Slab Gel Electrophoresis Unit (Hoefer Scientific Instruments). The gel dimensions were 10×9.5×0.075 cm. The DC power sources was an Electrophoresis power supply model EPS-301 (Amersham Pharmacia Biotech). Acrylamide and N,N-methylene bisacrylamide were obtained as a concentrated aqueous stock solution from Fluka AG. Ammonium persulfate (electrophoresis grade) was obtained from Sigma Chemical Co. Tetramethylethylenediamine (TEMED) (electrophoresis grade) and hemicals necessary for preparing buffers were of the highest purity available from BDH. The stock 0.90 M Tris-Borate-EDTA (TBE) buffer pH 8.3 and the loading buffer (30% glycerol, 0.025% bromophenol blue and 0.025% xylene cyanol FF in 90 mM TBE as well as the 20% polyacrylamide gel in 90 mM TBE was prepared according to the literature (see Essential Molecular Biology, A Practical Approach, Vol 1, Oxford, 1991, pp 89–126).

The sample was prepared by mixing calculated amounts of the fluorescent labelled $(dA)_{10}$ and PNA concentrated stock solutions in an Eppendorf tube to give the final total amounts of AMP ~1 nmol and the molar ratio of $F(dA)_{10}$:cPNA=1:1, 1:2, 1:3, 1:5 and 1:10. An appropriate volume of deionized water was added to give the final volume of 20 μL and an aliquot of the sample (10 μL, corresponding to 1 nmol dA nucleotide), was introduced into the well at the top of the gel by microsyringe. The system was connected to the power supply at 100 V until the bromophenol blue marker dye moved about half way through the gel (~2.5 h). The power supply was then disconnected and the gel was visualized by a UV transilluminator and photographs taken through a yellow filter with a digital camera (Kodak model DC240).

What is claimed is:

1. A compound of formula (I):

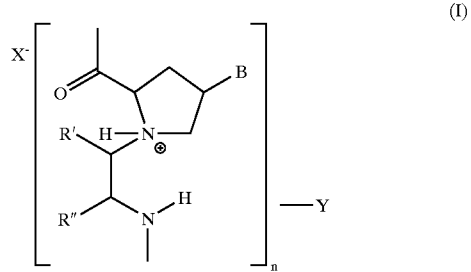

where n is 1 to 200,

B is a protected or unprotected base capable of Watson-Crick or of Hoogsteen pairing, X is OH or OR''' where R''' is a protecting group or an activating group or a lipophilic group or an amino acid or amino amide or nucleoside, Y is H or a protecting group or a lipophilic group or an amino acyl group or nucleoside and R' and R'', which are the same or different, are H, C1–C6 alkyl, aryl or aralkyl or R' and R'', together with the carbon atoms to which they are attached, form a cycloalkyl ring.

2. A compound as claimed in claim 1, of formula (II) or (III) where n, B, R', R'', X and Y are as defined in claim 1:

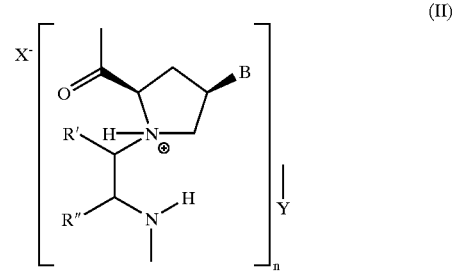

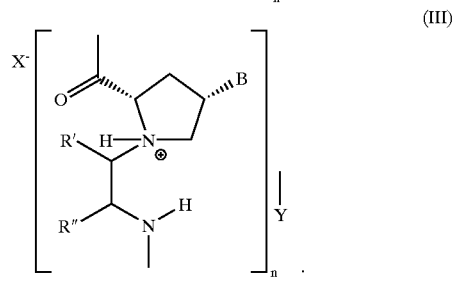

3. A compound according to claim 1, wherein B is a naturally occurring nucleobase selected from adenine, cytosine, guanine, thymine and uracil.

4. A compound according to claim 1, wherein X is OH and B is thymine and R' and R'' are H.

5. A compound according to claim 4, wherein Y if Fmoc.

6. A compound according to claim 1, wherein n is 1, B is a naturally occurring nucleobase selected from adenine, cytosine, guanine, thymine and uracil, and R' and R'' are H, X is OH or OR''', R''' is an activating group, and Y is H or a protecting group.

7. A compound according to any one of claims 1 to 5, wherein n is 5–30.

8. A hybrid comprising two strands of which a first strand is a compound according to claim 7 and a second strand is an oligo- or poly-nucleotide or nucleic acid.

9. A hybrid according to claim 8, wherein the two strands are hybridised to one another in a 1:1 molar ratio by base-specific Watson-Crick base pairing.

10. A pharmaceutical composition which comprises a compound as claimed in claim 1 and a pharmaceutically acceptable diluent or carrier.

* * * * *

UNITED STATES PATENT AND TRADEMARK OFFICE
CERTIFICATE OF CORRECTION

PATENT NO. : 6,716,961 B2
DATED : April 6, 2004
INVENTOR(S) : Lowe et al.

It is certified that error appears in the above-identified patent and that said Letters Patent is hereby corrected as shown below:

<u>Title page,</u>
Item [75], should read:

-- [75] Inventor: Gordon Lowe, Abingdon, Great Britain;
                          Tirayut Vilaivan, Bangkok, Thailand --

Signed and Sealed this

Fifteenth Day of June, 2004

JON W. DUDAS
*Acting Director of the United States Patent and Trademark Office*